United States Patent [19]

Chang et al.

[11] Patent Number: 5,728,915
[45] Date of Patent: Mar. 17, 1998

[54] TRANSGENIC MICE WHICH EXPRESS SIMIAN SV 40 T-ANTIGEN UNDER CONTROL OF THE RETINOBLASTOMA GENE PROMOTER

[75] Inventors: Long-Sheng Chang; Lingyun Zhu, both of Hilliard, Ohio

[73] Assignee: Children's Hospital, Inc., Columbus, Ohio

[21] Appl. No.: 436,730

[22] Filed: May 8, 1995

[51] Int. Cl.$^6$ .................... C07H 21/04; C12N 5/18; C12N 15/00
[52] U.S. Cl. .................. 800/2; 435/172.3; 435/354; 536/24.1
[58] Field of Search ................. 800/2; 514/44; 424/9.1; 435/240.21, 172.3, 354; 536/24.1

[56] References Cited

PUBLICATIONS

Teitz, T. et al (1994). DNA and Cell Biology 13, 705–710.
Wilkie, T. et al (1994). Oncogene 9, 2889–95.
Behringer, R. et al (1998). Proc.Natl. Acad. Sci USA 85, 2648–52.
Knowles, B. et al. (1990). Amer. Journal of Pathology 137, 259–262.
Bignon, Y–I et al (1993). Genes & Development 7, 1654–62.
T Ang. A et al (1989). Oncogene 4, 401–407.
Becerra, S. et al (1993) Journal of Biological Chemistry 268, 23, 148–56.
Noda, M.et al. (1988). Journal of Biological Chemistry 263, 13, 916–21.
Fields, B. et al. (1991) Fundamental Virology, 2$^{nd}$ ed. pp. 291, 319.
Ornitz et al (1987). Science 238, 188–93.
Zhu et al., 1995 "Regulational and Functional Analysis of the Human retinoblastoma susceptibility gene during development and tumorigenesis", Dissabs Accession No. 95:55830.

*Primary Examiner*—Brian R. Stanton
*Attorney, Agent, or Firm*—Vorys, Sater, Seymour and Pease

[57] ABSTRACT

Transgenic mice whose germ cells and somatic cells contain a simian SV40 T-oncogene operably linked to the promoter of the retinoblastoma susceptibility (RB) gene effective for expression of the T-oncogene in somatic cells of the mouse under control of the promoter spontaneously develop tumors of the ocular tissues as well as osteosarcomas and soft-tissue sarcomas. Such transgenic mice are useful as sources of tissue cultures of tumor cells and as animal models for the occurrence of osteosarcomas and soft-tissue sarcomas in humans and other animals.

5 Claims, 1 Drawing Sheet

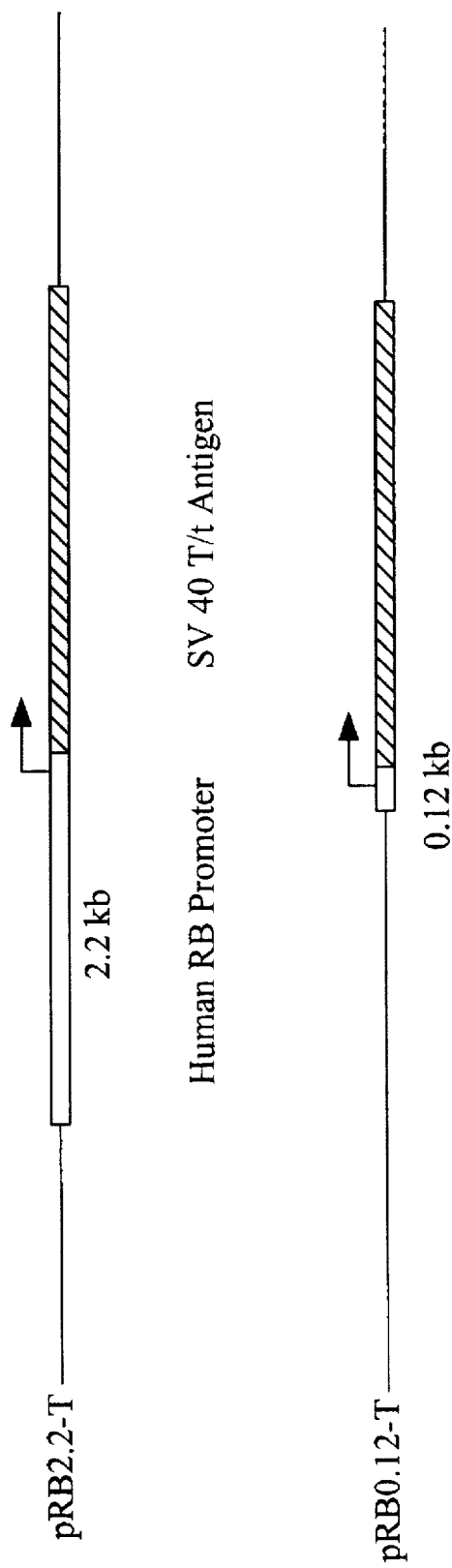

TRANSGENIC MICE WHICH EXPRESS SIMIAN SV 40 T-ANTIGEN UNDER CONTROL OF THE RETINOBLASTOMA GENE PROMOTER

BACKGROUND OF THE INVENTION

1. Field of the Invention

This invention relates to transgenic animals and more particularly to transgenic mice that spontaneously develop tumors of ocular tissue, bone tissue and soft tissues and are useful as models for osteosarcoma and soft-tissue sarcoma.

2. Brief Description of the Prior Art

The development of transgenic animals has provided biological and medical scientists with models that are useful in the study of disease. For example, Leder et al., U.S. Pat. No. 5,175,383, have disclosed an animal model for benign prostatic hyperplasia comprising a transgenic mouse containing in its somatic and germ cells a recombinant gene that predisposes the phenotype to spontaneous development of benign prostatic hyperplasia or hypertrophy. Such transgenic animals are useful in testing pharmaceutical agents for utility in treating the disease as well as in testing of compounds that might cause or promote the development of such diseases. Such animals are also useful as sources of cells for tissue culture that can be used to study the causes of a particular disease.

Some transgenic animals have been developed which have a tendency to develop spontaneous tumors. For example, Berns, U.S. Pat. No. 5,174,986, discloses a transgenic mouse predisposed to the development of lymphomas. Such animals are useful as test subjects for determining the oncogenic potential of chemical compounds or other carcinogenic agents such as murine leukemia viruses.

It is also known that the presence of certain defective genes in a cell can predispose the cell to tumor formation. Retinoblastoma, a cancer of the retina, is an intraocular malignancy which usually occurs in children under the age of four years at an incidence of one in about 20,000 live births. The tumor can be categorized as either sporadic (generally unilateral with a single focus of tumor formation) or heritable (frequently multifocal and bi-lateral). From genetic and epidemiological studies, Knudson, 1971, *Proc. Natl. Acad. Sci. USA* 68, pp.820-823, first proposed the "two-hit" hypothesis according to which two mutational events were required to induce malignant transformation. Subsequent studies confirmed that the loss or disabling of both alleles of a gene mapped to human chromosome 13 band q14 was required for the transformation. The inherited susceptibility to retinoblastoma arises from the loss of one allele, while the loss of the second allele due to mutation in a retinoblast cell results in its transformation into a tumor cell. The non-inherited form of the disease results from a random incapacitation of both alleles in a retinoblast cell. This gene, called the retinoblastoma susceptibility (RB) gene, encodes an mRNA of 4.7 kilobases that is usually mutated or deleted in tumor cells. The protein product encoded by the normal gene is a nuclear phosphoprotein (RB protein) with a molecular weight of about 105–110 kDa. All retinoblastoma cells tested to date fail to synthesize a normal-sized RB protein (Lee et al., 1987, *Nature*, 329, pp. 642–645). However, tumor formation is suppressed when the synthesis of RB protein is restored in human RB$^-$ tumor cells by inserting a normal RB gene. The RB protein binds to single-stranded and double-stranded DNA without sequence specificity, and is expressed in virtually all cell types examined to date. Furthermore, it is known to be phosphorylated, and thereby apparently inactivated, at the $G_1/S$ boundary of the cell cycle. Consequently, it is believed that the RB protein may play an important role in regulating cell growth in many cell types.

It has also been observed that patients who have a single RB mutation also have an increased risk of developing tumors at other, non-ocular sites. Such individuals are predisposed to a variety of second-site tumors, including osteosarcoma, soft-tissue sarcoma, and carcinomas of breast, lung, bladder and prostate. On the other hand, mutations in the RB gene have rarely or never been found in some other human tumors, such as colon carcinoma, melanoma, leukemia, neuroblastoma, and medulloblastoma. The details of this variable tissue-specific expression of the RB gene and the mechanism responsible for it are not understood.

Recently, the murine RB cDNA has been cloned, and the mouse RB protein showed 91% homology to the corresponding human protein (Bernards et al., 1989, *Proc. Nat. Acad. Sci. USA* 86, 6474–6478). Using this mouse cDNA as a probe, RB was found to be expressed early in mouse development, by at least day 11 of gestation. In adult mouse tissues, RB seems to be ubiquitously expressed. In order to determine the effect of deletion of one allele of the RB gene in mice, the embryonic stem cell-gene targeting technique was used to construct mouse strains in which one allele of the RB gene was disrupted (Clarke et al. *Nature* 323, pp. 328–330; Lee et al., 1992, *Nature* 359, pp. 288–294). Surprisingly, heterozygous mice did not develop retinoblastoma, but later developed a pituitary tumor. Embryos homozygous for the RB mutation died between days 14 and 15 of gestation, exhibiting neuronal cell death and defective erythropoiesis. These results suggest that RB plays an important role in the early development of the mouse. However, they shed no light on the possible role of RB in controlling differentiation of retinoblasts and other tissues at later stages of mouse development.

In another line of investigation of the effect of RB protein on the development of tissues, it has been shown that the SV40 T-antigen can bind to RB protein, thereby preventing it from performing its cell cycle-controlling function (DeCaprio et al., 1988, *Cell* 54, pp. 275–283). When such binding occurs, the cell is transformed, and proliferates without control.

Transgenic mouse technology has been used to study the tissue specificity of a cloned gene and offers the distinct advantage over experiments in tissue culture that expression of a transgene can be surveyed in all cell types in vivo. However, efforts to identify tissue-specific regulatory elements of the RB gene have been hampered by lack of appropriate tissue culture systems.

Accordingly, a need has continued to exist for an animal model that can help to elucidate the tissue-specific expression of regulatory elements for the RB gene throughout the life of the animal.

SUMMARY OF THE INVENTION

Transgenic mice have now been produced that incorporate the regulatory portion of the RB gene in germ cells and somatic cells combined with a reporter gene that can help to identify the somatic cells in which the RB gene is expressed. The genome of such mice contains the SV40 T-antigen oncogene under the control of at least a fragment of the promoter region of the human RB gene. When a 2.0-kb DNA segment containing the human RB promoter sequence is linked to the SV40 T-antigen coding region and used in the production of trangenic mice, the transgenic animals develop tumors in certain tissues in which the SV40 T-antigen is expressed under control of the human RB promoter. In particular, such transgenic mice are prone to develop tumors in the eye as well as in the pineal gland, the heart and colon. When a 0.12-kb fragment of the human RB promoter sequence, containing only the 119 base pairs at the 3'-end of the 2.0-kb segment, is fused to the SV40 T-antigen encoding region and used to produce transgenic mice, a line of transgenic mice is obtained which do not exhibit eye defects, but surprisingly develop osteosarcomas or soft tissue sarcomas at an age of about 3–7 months.

Accordingly, it is an object of the invention to provide a transgenic animal suitable as a model for tumor development.

A further object is to provide a transgenic animal that expresses SV40 T-antigen under control of at least a portion of the human RB promoter sequence.

A further object is to provide a transgenic animal that can be a source of cells for tissue culture containing SV40 T-antigen under control of the human RB promoter.

A further object is to provide a transgenic animal that spontaneously develops tumors characteristic of loss of the retinoblastoma (RB) gene function.

A further object is to provide a transgenic animal that spontaneously develops osteosarcomas and soft-tissue sarcomas.

Other objects of the invention will become apparent from the description of the invention which follows.

BRIEF DESCRIPTION OF THE DRAWINGS

FIG. 1: The sole FIGURE is a diagrammatic representation of the region of plasmid pRB2.0-T containing the SV40 T-antigen coding sequence coupled to the 2.0 kb segment of the RB promoter control sequence, and the region of plasmid pRB0.2-T containing the SV 40 T-antigen coding sequence coupled to the 0.2 kb segment of the RB promoter control sequence.

DETAILED DESCRIPTION OF THE INVENTION AND PREFERRED EMBODIMENTS

In order to prepare a transgenic mouse in which the regulation of the expression of the RB gene in different tissues in vivo could be determined, the simian virus SV40 T-antigen encoding gene was linked to the human RB promoter region and used in the production of transgenic mice. Two specific sequences of the human RB gene were linked to the simian SV40 T-antigen encoding gene: 1) a 2.0-kb region that is believed to encompass the essential promoter function (T'Ang et al., 1989, *Oncogene* 4, pp. 401–407), and 2) a 0.12-kb fragment constituting the 119-base pair segment at the proximal end of the 2.0-kb promoter sequence. These two sequences were linked to the simian SV40 T-antigen encoding sequence, and the constructs were used to prepare transgenic mice.

It was found that those mice containing the 2.0-kb segment of the human RB promoter linked to the SV40 T-antigen gene produced very few viable offspring. Of the four mice that were produced, one was found to contain only a single copy of the RB-SV40 T-antigen gene. This mouse did not show any abnormalities, and its progeny also exhibited a normal phenotype. Three of the mice containing the SV40 T-antigen gene under control of the RB promoter contained multiple copies of the transgene. These mice exhibited severe abnormalities of the eye, and two of the three mice died at 18 and 19 days after birth, respectively, without opening their eyes. The third mouse bearing multiple copies of the transgene survived for a longer period. However, its eyes also were very abnormal, and, after its condition was observed to deteriorate, it was sacrificed and its tissues subjected to histopathological examination. It was found to have developed tumors in the eye, pineal gland, mid-brain, heart and colon. The eye tumor cells were tumorigenic when tested in nude mice. Tissue cultures prepared from the tumors of the eye, heart and brain were found to express the transgene encoded T-antigen.

In contrast to the transgenic mice bearing the 2.0-kb RB promoter segment, the mice that received the RB0.12-T gene construct were generally healthy, and several transgenic mice were obtained. These mice did not develop retinoblastoma tumors. However, unexpectedly, they developed abnormalities at an age of 3–7 months that were shown by histopathological investigation to be due to osteosarcomas and soft-tissue sarcomas. The founders passed the tumor-forming tendency to their offspring, showing that the gene was integrated into the germ line. Consequently, a strain of transgenic mice has been developed which exhibits the property of uniformly developing osteosarcomas and soft-tissue sarcomas at a certain age.

Plasmid construction and DNA preparation:

To construct the pRB2.0-T plasmid the p4-14-5BB plasmid containing the promoter region and the first exon of the human RB genome DNA (T'ang, et al., 1989, *Oncogene* 4, pp. 410–407) was digested with BssH II enzyme (at 59 bases upstream of the translation initiation codon) and BamH I enzyme which cut at 2.0 kb upstream (Lee et al., 1987, *Science* 235, pp. 1394–1399). The 2.0-kb promoter fragment was then treated with $T_4$ DNA polymerase to fill in the ends and subcloned into pKS(+) at the Hinc II site to generate the pKS(+)/RB plasmid. To obtain the T-antigen coding region the pW2 plasmid containing the Hpa II-BamH I SV40 early-antigen coding region was first digested with BamH I and then partially digested with Hind III. A 2.6-kb T-antigen DNA segment containing the SV40 sequence for nucleotide number 5171 to 2533 was eluted and cloned into the pKS(+)/BB plasmid which was digested by the Hind III and BamH I enzymes. The resulting hybrid plasmid, pRB2.0-T, contains the SV40 T-antigen coding region placed under control of the 2.0-kb human RB promoter sequence (FIG. 1). The pRB0.12-T plasmid was constructed by removing the RB promoter upstream sequence between the BamH I and Sac II sites (located at 178 bases upstream of the initiation codon) from the pRB2.0-T plasmid. This plasmid contains only 0.12 kb of the RB promoter DNA and appears to be able to function as a minimal promoter when tested in transfection experiments. Both plasmids were first tested for their ability to transform cultured rodent cells as described previously by Chang et al., 1984, *Virology* 133, pp. 341–353, and then used in the transgenic experiments. In brief, the DNAs containing the RB promoter-driven T expression cassettes were separated from the vector sequence by appropriate restriction digestions and electroeluted onto a dialysis membrane (Sambrook et al., 1989, *Molecular Cloning: A Laboratory Manual*, Cold Spring Harbor Laboratory, Cold Spring, N.Y.). The eluted DNA was further washed and cloned by spinning through an Amicon-10 microconcentrator. The amount of the eluted DNA was quantitated by agarose gel electrophoresis.

Microinjection and production of transgenic mice:

Inbred mouse strains, FVB/N and C57BL/6J (Taketo et al., 1991, *Proc. Natl. Acad. Sci. USA* 88:2065–2069) were used in the transgenic experiments. Embryos were obtained from superovulated females and microinjections were performed by standard techniques as described by Hogan et al., 1986, *Manipulating the Mouse Embryo: A Laboratory Manual*, Cold Spring Harbor Laboratory, Cold Spring, N.Y. Mice were maintained on a cycle of light from 6:00 a.m. to 6:00 p.m. Superovulation was induced by intraperitoneal injection of 5 international units each of pregnant mare serum and human chorionic gonadotropin with 48 hours interval. All DNAs for microinjection were suspended in the microinjection buffer (10 mM Tris-HCl/0.1 mM EDTA, pH 7.4) to a concentration of 1–10 ng/microliter. Embryos that survived microinjection were reimplanted the same day into the oviducts of pseudopregnant CD1 females that had been randomly mated to vasectomized B6D2F1 males to allow complete development to term. Positive transgenic founders ($F_0$) were bred according to Hogan et al., 1986, and mated to either FVB/N or C57BL/6J mice to generate $F_1$ offsprings. $F_2$ or $F_3$ offsprings were also generated by a similar procedure.

Transgenic mice containing the RB2.0-T transgene:

Although the RB2.0-T DNA gave very low transgenic efficiency, a few transgenic mice were produced, all of which exhibited eye defects at birth.

A total of 1679 fertilized eggs isolated from FVB/N× FVB/N mice were injected with 6 preparations of RB2.0-T DNA at various concentrations (1–10 ng/μL). These injected embryos were transferred to 78 foster mothers. A large proportion of these transgenic embryos did not develop to full term, and about 50% of the foster mothers did not deliver any mice. Surgical examination of the foster mothers revealed that most of these injected embryos died in the embryonic stage. Since the dead embryos were reabsorbed by the uterus and it was difficult to determine which embryos carried the transgene, it was not possible to determine at what stage of the embryonic development the transgenic embryos were blocked. These results suggest that expression of the T-antigen oncoprotein from the RB2.0-T fusion gene early during embryonic development may be lethal to the mouse.

From the 1679 eggs injected with the RB2.0-T DNA, 171 newborns were delivered by the foster mothers. Southern blot analysis was performed on tail DNA from 164 of these (7 having died shortly after birth) in order to identify any positive transgenic mice. Four independent transgenic founders ($F_0$) were identified from this analysis. Tail DNAs from these four mice, digested with EcoR I enzyme, which does not cut at the transgene, contained hybridizing bands larger than the size of the transgene. Densitometer tracings of the radioactivity of the hybridizing bands and comparison with the intensity of a single-copy gene using the c-myc gene as a control revealed that one of the mice (#32) contained a single copy of the transgene, while the other three positive mice contained multiple copies of the transgene integrated into the genome.

The mouse bearing only a single copy of the transgene did not show any visible abnormality. It transmitted the transgene to about 50% of its immediate offspring, and these animals also appeared to be normal. While these mice did not exhibit any abnormality or tendency to develop disease conditions as they grew older, they do provide a pool of animals that contain the SV40 T-antigen gene under control of the RB promoter. Consequently, they can be useful in preparing further trangenic animals that may incorporate other transgenes that may interact with the SV40 T antigen gene.

The other three transgenic animals containing the RB2.0-T transgene were shown to have multiple copies of the transgene integrated into the mouse genome. These animals exhibited frank pathology at birth and afterward. Initially they were physically smaller than the transgene-negative mice. Unlike normal mice whose eyes open at an age of about two weeks, two of these animals, who died at 18 and 19 days after birth, respectively, never opened their eyes.

The third animal bearing multiple transgenes (#374) survived for 40 days, at which time its condition dramatically deteriorated, and it was sacrificed for histopathological examination. The left eye of this mouse did not open at all;, the right eye opened only partially, and its eyeball was not translucent. Histopathological examination showed that both eyes of this mouse contained tumors, located in the retinal region. Because the tumor cells were very undifferentiated, it was not possible to characterize the original cell type. However, some characteristics of retinoblastoma such as a rosette-like structure were noted by electron microscopy. A tumor, also of very undifferentiated cells, was found in the pineal gland of the mid-brain, and tumors were also found in the heart and colon. Hydronephroses of undetermined cause was also observed. The remaining tissues showed no pathological abnormalities.

A portion of the tumor tissue from one of the eyes of this mouse was taken for tissue culture and used for a tumorigenicity experiment and for biochemical analysis. About $10^5$ cultured eye tumor cells were injected subcutaneously or into the front chamber of the eye of nude mice. Tumor masses could be readily detected at the site of injection or in the injected eye two months after injection. These results demonstrate that a tumorigenic cell culture can be obtained from transgenic mice of this invention.

To detect the expression of the transgene-encoded T-antigen in various tissues of this mouse, Western blot analysis using the anti-T monoclonal antibody pAb419 was conducted. High levels of T-antigen were found to be expressed in the eye, heart, and brain, but very little of the T-antigen was expressed in the bone, intestine, lung, spleen kidney or liver. To detect the endogenously expressed RB protein, a similar Western blot analysis was conducted using the anti-RB monoclonal antibody mAb245. As has been previously reported (Bernards et al., 1989, *Proc. Natl. Acad. Sci. USA* 87, pp. 7762–7766) RB was found to be expressed in all the mouse tissues examined, although the level of expression appeared to vary considerably among the different tissues.

Transgenic mice containing the RB0.12-T transgene:

The pRB0.12-T plasmid, which contained the 119-bp 3'-terminal of the human RB promoter was used to prepare transgenic mice by the procedure described above. Because the FVB/N mice used in the experiments are known to carry a recessive mutation at the retinal degeneration (rd) locus (Taketo et al., 1991), transgenic RB0.12-T mice with a wild-type rd background were also prepared using embryos from mating of the C57BL/6J (+/+) and FVB/N (rd/rd) mice. The RB0.12-T DNA gave rise to viable transgenic mice with practical efficiency. A total of 208 embryos injected with the RB0.12-T construct were transferred to 9 foster others. A total of 48 newborns were delivered. Southern blot analysis of the mouse tail DNAs identified 8 positive transgenic RB0.12-T mice. Four of these founders ($F_0$) were agouti (from mating of C57BL/6J×FVB/N) and the other 4 were white (FVB/N×FVB/N). The transgenic efficiency of the RB0.12-T construct appeared to be independent of the rd background. Densitometer tracing of the radioactivity of the hybridizing bands in the southern blot showed that all of these mice contained multiple copies of the transgene integrated into the mouse genome. All of the transgenic RB0.12-T mice appeared normal at birth, and they opened their eyes at about the same time as their transgene-negative littermates. All of the $F_0$ mice transmitted their transgene to their offspring in a Mendelian fashion. In addition, several generations of offspring ($F_{1-4}$) were produced, and all appeared normal at an early age.

Surprisingly, however, the mice carrying the RB0.12-T construct manifested an abnormality after 3–7 months of age. Two typical abnormalities could be observed. A majority of the mice developed a symptom with difficulty in the movement of their head and neck. A twist, either left or right, could be observed in these mice. The other type of abnormality observed was a shrunken body. The appearance of these mice was similar to that of dwarf mice with a small body as compared to transgene-negative littermates of the same age. Some of these shrunken-body mice also developed the problem with movement of their head and neck. These abnormalities were observed in both the agouti (C57BL/6J×FVB/N) and white (FVB/N×FVB/N) mice, and were observed in both sexes. The abnormal phenotype was observed in almost all transgenic RB0.12-T founders and their offspring after 3–7 months of age.

Upon histopathological examination of these transgenic RB0.12-T mice with symptoms of either twisted head or shrunken body, all of them showed the presence of some tumor mass(es) in their bodies. The majority of the histological types of these tumor masses was osteosarcoma and the most common anatomical sites at which these tumors were observed were in the brain and/or periosteal bone. Some animals with soft-tissue sarcomas or undifferentiated malignancy were also observed. These pathological symptoms appear to be genetically transmittable, and were observed up to the $F_2$ generation.

To determine whether the T-antigen was expressed in the transgenic RB0.12-T mice, Western blot analysis on the protein extracts prepared from various mouse tissues were conducted using the anti-T monoclonal antibody pAb419. When the protein extracts were prepared from tissues of a transgenic RB0.12-T mouse of age 40 days (at that time the mouse did not show any abnormality), no T-antigen was detected in any of the tissues examined. However, when protein extracts were prepared from tissues of a transgenic RB0.12-T mouse of age about 4 months, T-antigen expression could be detected in the tissues that contained tumor lesions.

Southern blot analysis of mouse tail DNAs:

Mouse tail DNAs were prepared by a slightly modified procedure of Hogan et al., 1986. Briefly, at the time of weaning (2–3 weeks of age) about 1 cm of the tail was cut from each mouse of the new litter and placed in a 2-ml microfuge tube containing 0.6 ml of tail-DNA extraction buffer (10 mM Tris-HCl, pH 8, 100 mM EDTA, 0.5% SDS, 20 microgram/ml pancreatic RNase, and 100 microgram/ml Proteinase K). The tail-buffer mixture was incubated at 55° C. overnight and then cooled to room temperature. An equal volume of buffer-saturated phenol was added and the entire mixture was mixed by gently inverting the tube back and forth for 5 minutes. The DNA phase was separated by centrifugation and transferred to another tube. The extraction was repeated once more and the resulting DNA solution was further extracted with chloroform twice. After the final round of chloroform extraction, 0.2 volumes of 10M ammonium acetate and 2 volumes of ice-cold ethanol were added and mixed several times by inverting the tube until a stringy white precipitate formed. The stringy precipitate was removed by touching it to the sealed end of a Pasteur pipette. The spooled DNA was dipped into ethanol several times and then transferred to another tube. The DNA was dried briefly and resuspended in 0.5 ml of 1×TE buffer (10 mM Tris-HCl/1 mM EDTA, pH 7.4). The DNA concentration of the solutions was determined by measuring the $OD_{260}$ and $OD_{280}$ of each solution. Transgenic mice were identified by Southern blot analysis as described by Sambrook et al., 1989. Ten micrograms of each of the mouse tail DNAs were first digested with EcoRI restriction enzyme, fractionated onto a 0.7% agarose gel, and then transferred to a Gene-ScreenPlus™ hybridization transfer membrane (NEN, Massachusetts). The membrane was UV-crosslinked, baked at 80° C. for 2 hours, and then hybridized with a random-primed labeled SV40 T-antigen probe. Quantitation of the copy number of the transgene was done by densitometry of the autoradiogram with a Betascope 603 Blot analyzer (Betagene, Massachusetts). Positive transgenic mice were selected and closely watched for any visible pathological abnormality. In addison, these positive mice were mated for production of offsprings for further analysis.

Histopathological examination of mouse tissues:

Positive transgenic mice were examined for visible abnormalities routinely. On some occasions a special animal ophthalmoscope was used for gross examination to detect any specific abnormality in the mouse eyes. All mice with visible abnormalities and some without visible abnormalities were first examined anatomically following cervical dislocation. To preserve fine structure of the eye some mice were anesthetized and perfused with glutaraldehyde introduced into an artery from the jugular artery ascending through the mouse head before examination. Histological and pathological examination was performed on some normal tissues as well as of all types of tumor tissues observed in the transgenic mice. Surgically removed tissues were fixed in 10% neutral buffered formalin and then embedded in paraffin. Thin sections of each tissue were obtained by a Microm rotary microtome HM 330, stained with hematoxylineosin, and examined with a Nikon microscope.

Culture of eye tissue and injection into nude mice:

Eye tumor tissue was aseptically removed from the transgenic mouse #374 and washed in a sterile dish containing phosphate buffered saline with penicillin and streptomycin. The tissue was minced into small pieces with a pair of iris scissors and transferred to a sterile centrifuge tube. The tube containing eye tissue cells was spun at a low speed (800 RPM) in a Sorvall RC3C centrifuge. The supernatant was removed by suction and the eye tissue cells were resuspended in RPMI medium supplemented with 15% fetal bovine serum. These eye tissue cells were cultured at 37° C. with 5% $CO_2$ in a humidified incubator. For the tumorigenicity test, about $10^5$ cultured eye tumor cells were injected subcutaneously or into the front chamber of the eye in nude mice as described by White et al., 1989. Eye tumor cells grown from the dishes were subcultured once and then used in the immunoprecipitation and Western blot experiments as described previously.

Immunoprecipitation and Western blot analysis:

Monoclonal antibody against T-antigen (pAb419), monoclonal antibody against p53 (pAB421), and monoclonal antibodies against RB protein (mAb245 and XZ56) were used in the immunoprecipitation experiments. Cultured eye tumor cells were metabolically labeled with 0.5 mCi/ml of Trans-S$^{35}$-Label (ICN Biochemicals, Inc., California) for 4 hours at 37° C. and then harvested for immunoprecipitation (Harlow et al., 1986, *Mol. Cell. Biol.* 6, pp. 1579–1589; DeCaprio et al., 1988, *Cell* 56, pp. 1085–1095; Hu et al., 1991, *Mol. Cell. Biol.* 11, pp. 5792–5799). The immune complexes were pulled down by protein A-Sepharose 4B beads (Zymed Laboratories, Inc., California), washed, and transferred by electrophoresis onto an SDS polyacrylamide gel.

For Western blot analysis dissected mouse tissues were frozen immediately in liquid nitrogen and then stored at –80° C. The tissues were lysed and sonicated in 1–2 ml of the lysis buffer (50 mM HEPES, pH 7.0, 250 mM NaCl, and 0.1% NP40). The tissue lysates were clarified by centrifugation at 2500 RPM for 5 min at 4° C. The concentration of the soluble proteins in each clear lysate was determined by using the Bio-Rad protein assay dye solution (Bio-Rad Laboratories, California). Equal amounts of protein (100–200 micrograms) from each tissue lysate were run onto an SDS-polyacrylamide gel and transferred to an Immobilon membrane (Millipore, Massachusetts). The T-antigen on the filter was detected by using the ProtoBlot Western Blot AP system (Promega Corporation, Wisconsin) containing alkaline phosphatase-conjugated antimouse immunoglobulin secondary antibody.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A transgenic mouse whose germ cells and somatic cells contain an SV40 T-antigen oncogene which is operably linked to a fragment of the promoter sequence of a human retinoblastoma susceptibility gene which is a 119-base sequence between the Sac II and BamH I restriction sites of said promoter sequence, said SV40 T-antigen oncogene and said operably linked fragment of said promoter sequence being introduced into said mouse or an ancestor of said mouse at an embryonic stage and being effective to produce osteosarcomas or soft-tissue tumors in said mouse when said SV40 T-antigen oncogene is expressed.

2. A tumor-cell culture prepared from an osteosarcoma of the transgenic mouse of claim 1, wherein cells of said tumor cell culture contain said SV40 T-antigen oncogene operably linked to said fragment of said promoter sequence.

3. A tumor-cell culture prepared from a soft-tissue sarcoma of the transgenic mouse of claim 1, wherein cells of said tumor cell culture contain said SV40 T-antigen oncogene operably linked to said fragment of said promoter sequence.

4. A transgenic mouse whose germ cells and somatic cells contain an SV40 T-antigen oncogene which is operably linked to a fragment of the promoter sequence of a human retinoblastoma susceptibility gene which is a 2.0 kilobase sequence between the BssH II and BamH I restriction sites of said promoter sequence, said SV40 T-antigen oncogene and said operably linked fragment of said promoter sequence being introduced into said mouse or an ancestor of said mouse at an embryonic stage and being effective to produce ocular tumors in said mouse when said SV40 T-antigen oncogene is expressed.

5. A tumor-cell culture prepared from an ocular tissue tumor of the transgenic mouse of claim 2, wherein cells of said tumor cell culture contain said SV40 T-antigen oncogene operably linked to said fragment of said promoter sequence.

* * * * *

UNITED STATES PATENT AND TRADEMARK OFFICE
CERTIFICATE OF CORRECTION

PATENT NO.    : 5,728,915
DATED         : March 17, 1998
INVENTOR(S)   : Long-Sheng Chang et al.

It is certified that error appears in the above-identified patent and that said Letters Patent is hereby corrected as shown below:

Column 1,
Line 5, after the title, insert the following paragraph:
-- This invention was made with Government support under Grant No. R 29 CA 54323 and 1P20 NS 31087 awarded by the National Institutes of Health. The United States government may own certain rights in the invention. --

Signed and Sealed this

Fourteenth Day of October, 2003

JAMES E. ROGAN
*Director of the United States Patent and Trademark Office*